(12) United States Patent
Podhipleux et al.

(10) Patent No.: US 7,713,550 B2
(45) Date of Patent: May 11, 2010

(54) CONTROLLED RELEASE SODIUM VALPROATE FORMULATION

(75) Inventors: Nilobon Podhipleux, Weston, FL (US); Xiu Xiu Cheng, Weston, FL (US); Unchalee Lodin, North Miami Beach, FL (US); Chih-Ming Chen, Taipei (TW); Avinash Nangia, Weston, FL (US); Dacheng Tian, Miramar, FL (US)

(73) Assignee: Andrx Corporation, Plantation, FL (US)

( * ) Notice: Subject to any disclaimer, the term of this patent is extended or adjusted under 35 U.S.C. 154(b) by 763 days.

(21) Appl. No.: 10/868,286

(22) Filed: Jun. 15, 2004

(65) Prior Publication Data

US 2005/0276850 A1    Dec. 15, 2005

(51) Int. Cl.
*A61K 9/20* (2006.01)
*A61K 9/24* (2006.01)
*A61K 9/28* (2006.01)
*A61K 9/30* (2006.01)

(52) U.S. Cl. ............... 424/473; 424/464; 424/465; 424/472; 424/474; 424/475

(58) Field of Classification Search .......... None
See application file for complete search history.

(56) References Cited

U.S. PATENT DOCUMENTS

| | | | |
|---|---|---|---|
| 3,133,132 A | 5/1964 | Loeb et al. ............... 264/49 |
| 3,173,876 A | 3/1965 | Zobrist .................... 252/137 |
| 3,276,586 A | 10/1966 | Rosaen .................... 210/90 |
| 3,325,361 A | 6/1967 | Meunier et al. ........... 167/65 |
| 3,541,006 A | 11/1970 | Bixler et al. .............. 210/23 |
| 3,541,055 A | 11/1970 | Malamet et al. .......... 260/78.4 |
| 3,546,142 A | 12/1970 | Michaels et al. .......... 260/2.1 |
| 3,845,770 A | 11/1974 | Theeuwes et al. ......... 128/260 |
| 3,865,108 A | 2/1975 | Hartop ..................... 128/260 |
| 3,916,899 A | 11/1975 | Theeuwes et al. ......... 128/260 |
| 4,002,173 A | 1/1977 | Manning et al. .......... 128/296 |
| 4,008,719 A | 2/1977 | Theeuwes et al. ......... 128/260 |
| 4,034,758 A | 7/1977 | Theeuwes ................. 128/260 |
| 4,036,228 A | 7/1977 | Theeuwes ................. 128/260 |
| 4,063,064 A | 12/1977 | Saunders et al. .......... 219/121 |
| 4,077,407 A | 3/1978 | Theeuwes et al. ......... 128/260 |
| 4,088,864 A | 5/1978 | Theeuwes et al. ......... 219/121 |
| 4,207,893 A | 6/1980 | Michaels .................. 128/260 |
| 4,558,070 A | 12/1985 | Bauer et al. .............. 514/557 |
| 4,601,894 A * | 7/1986 | Hanna et al. .............. 424/480 |
| 4,699,927 A | 10/1987 | Deboeck ................... 514/564 |
| 4,783,337 A | 11/1988 | Wong et al. ............... 424/468 |
| 4,895,873 A | 1/1990 | Shaäfer .................... 514/557 |
| 4,913,906 A | 4/1990 | Friedman et al. .......... 424/499 |
| 4,940,580 A * | 7/1990 | Sangekar et al. .......... 514/166 |
| 4,988,731 A | 1/1991 | Meade ..................... 514/557 |
| 5,017,613 A | 5/1991 | Aubert et al. ............. 514/557 |
| 5,049,586 A | 9/1991 | Ortega et al. ............. 514/557 |
| 5,071,607 A | 12/1991 | Ayer et al. ................ 264/112 |
| 5,169,642 A | 12/1992 | Brinker et al. ............ 424/488 |
| 5,185,159 A | 2/1993 | Aubert et al. ............. 424/489 |
| 5,212,326 A | 5/1993 | Meade ..................... 562/606 |
| 5,681,582 A * | 10/1997 | Gilis et al. ................ 424/468 |
| 5,707,663 A * | 1/1998 | Ayer et al. ................ 424/473 |
| 5,807,574 A | 9/1998 | Cheskin et al. ............ 424/451 |
| 5,980,943 A * | 11/1999 | Ayer et al. ................ 424/470 |
| 6,077,542 A | 6/2000 | Sherman .................. 424/489 |
| 6,096,339 A | 8/2000 | Ayer et al. ................ 424/473 |
| 6,106,863 A * | 8/2000 | Ukigaya et al. ........... 424/480 |
| 6,287,598 B1 | 9/2001 | Ayer et al. ................ 424/468 |
| 6,352,721 B1 * | 3/2002 | Faour ...................... 424/473 |
| 6,365,185 B1 * | 4/2002 | Ritschel et al. ........... 424/473 |
| 6,419,953 B1 | 7/2002 | Qin et al. ................. 424/465 |
| 6,491,949 B2 * | 12/2002 | Faour et al. ............... 424/473 |
| 6,528,090 B2 * | 3/2003 | Qiu et al. ................. 424/464 |
| 2001/0005512 A1 | 6/2001 | Anderson ................. 424/464 |
| 2005/0048120 A1* | 3/2005 | Edgren et al. ............. 424/473 |

FOREIGN PATENT DOCUMENTS

WO    9427587 A2    12/1994
WO    0037055 A1    6/2000

OTHER PUBLICATIONS

Depakote® Er, Physician's Desk Reference(2002) pp. 436-438.

* cited by examiner

*Primary Examiner*—S. Tran
(74) *Attorney, Agent, or Firm*—Hedman & Costigan, P.C.

(57) ABSTRACT

Disclosed is a controlled release formulation comprising valproic acid, pharmaceutically acceptable salt thereof, amide thereof, or derivative thereof.

3 Claims, 5 Drawing Sheets

Figure 1. Dissolution Profile of Sodium Valproate XT Tablets, 576 mg in pH 7.5 Phosphate Buffer Displaying Original Release Data vs. Re-lease Data (Paddle method at 75 rpm).
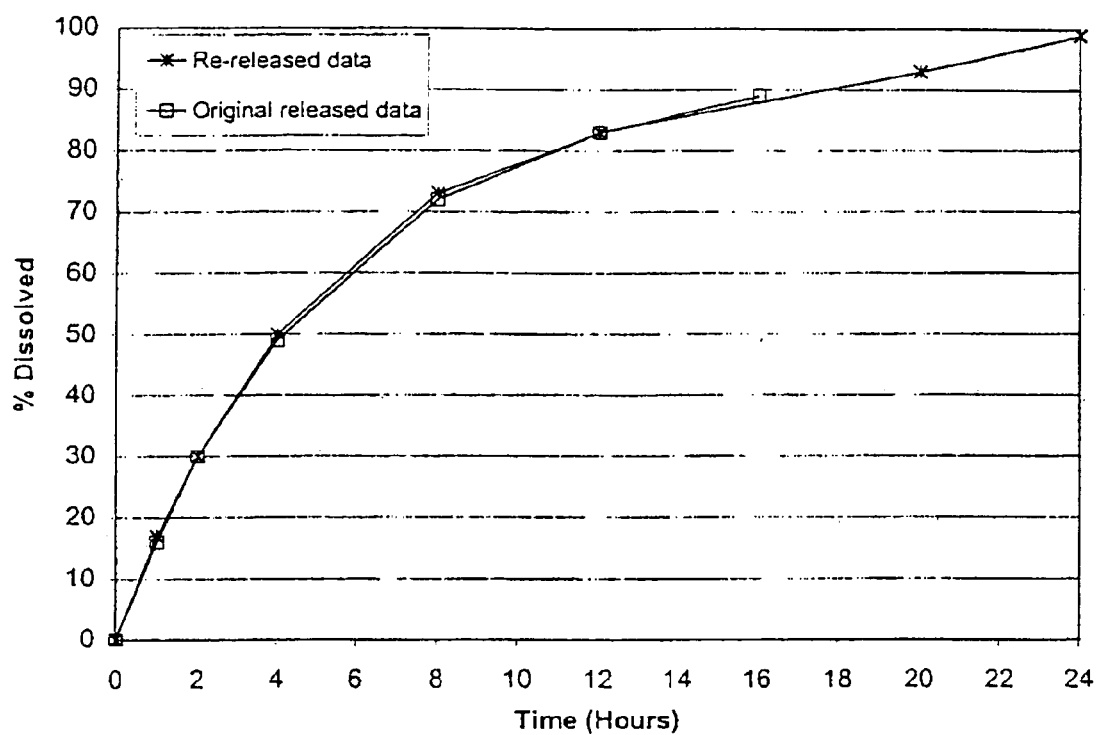

Figure 2. Dissolution Profile of Sodium Valproate XT Tablets, 576 mg in pH 7.5 Phosphate Buffer (Paddle method at 75 rpm vs. Basket method at 100 rpm).
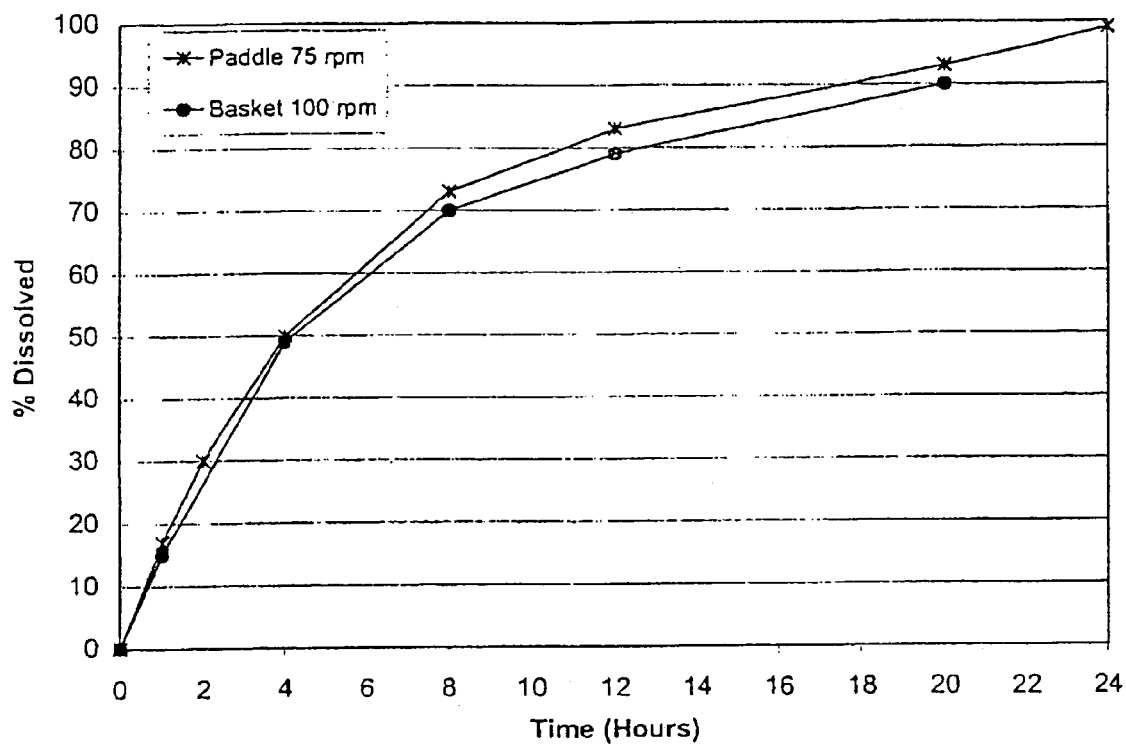

Figure 3. Dissolution Profile of Sodium Valproate XT Tablets, 576 mg and Depakote® ER Tablets, 500 mg in pH 7.5 Phosphate Buffer (Basket method at 100 rpm).
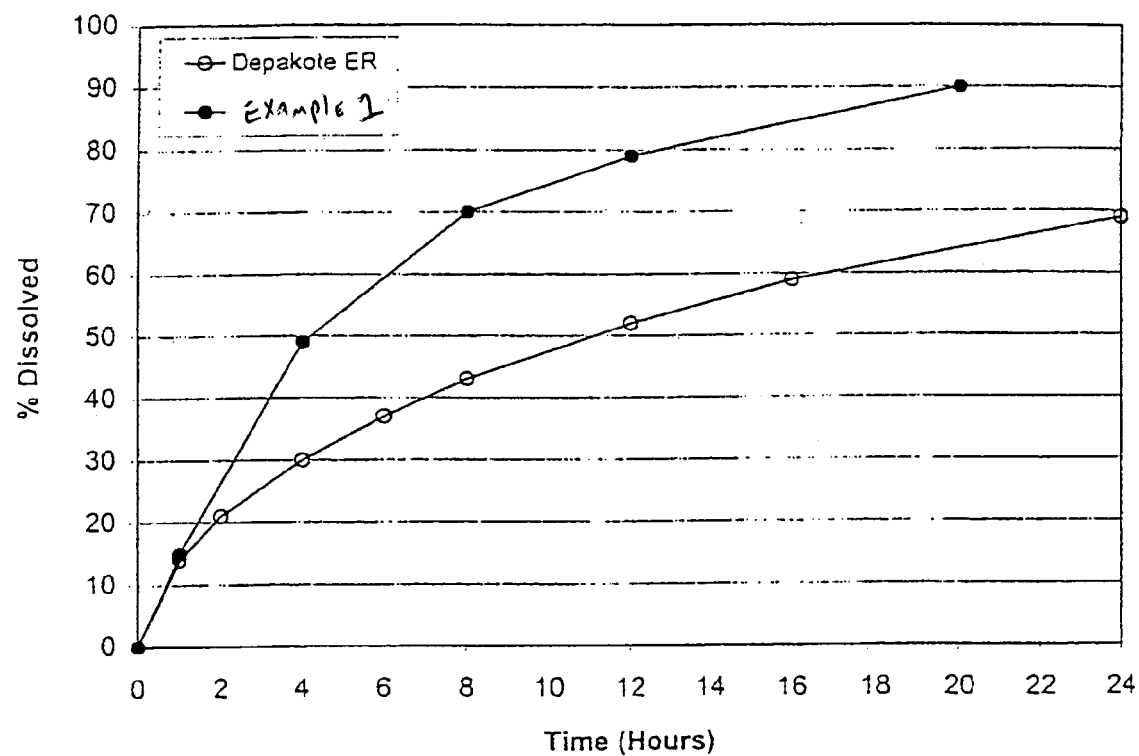

Figure 4. Dissolution Profile of Depakote® ER, 500 mg in SGF, pH 4.2 Acetate Buffer and pH 7.5 Phosphate Buffer (Basket method at 100 rpm).
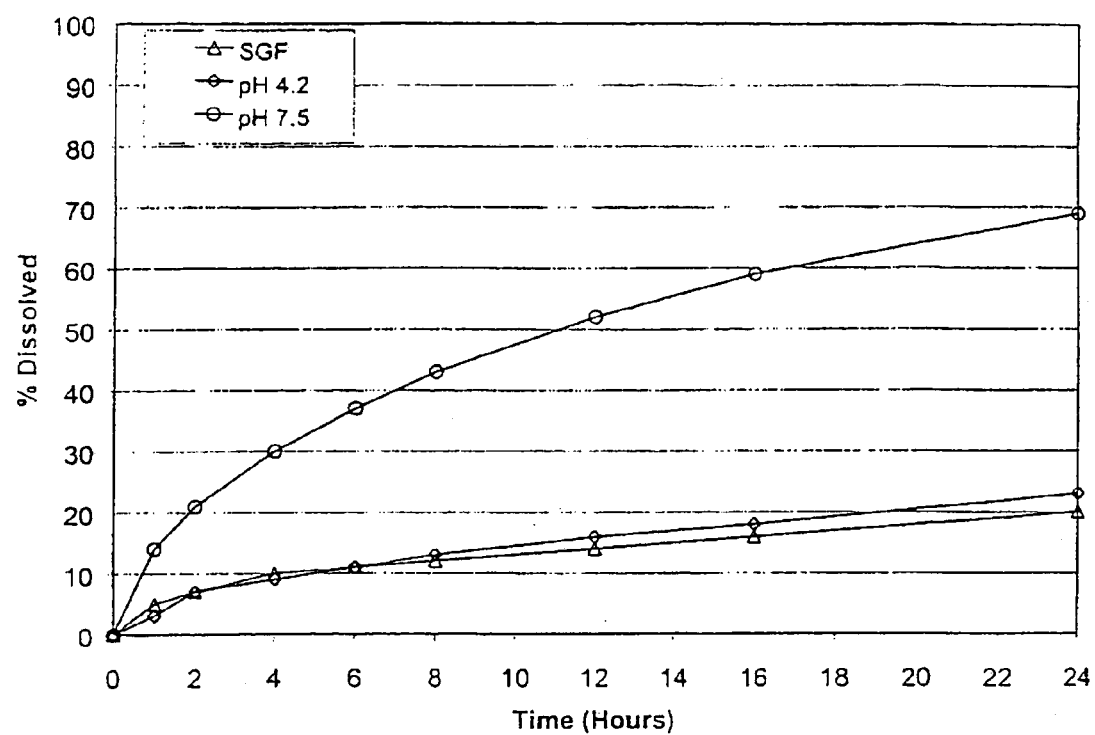

Figure 5. Dissolution Profile of Sodium Valproate XT Tablets, 576 mg in SGF, pH 4.2 Acetate Buffer and pH 7.5 Phosphate Buffer (Basket method at 100 rpm).
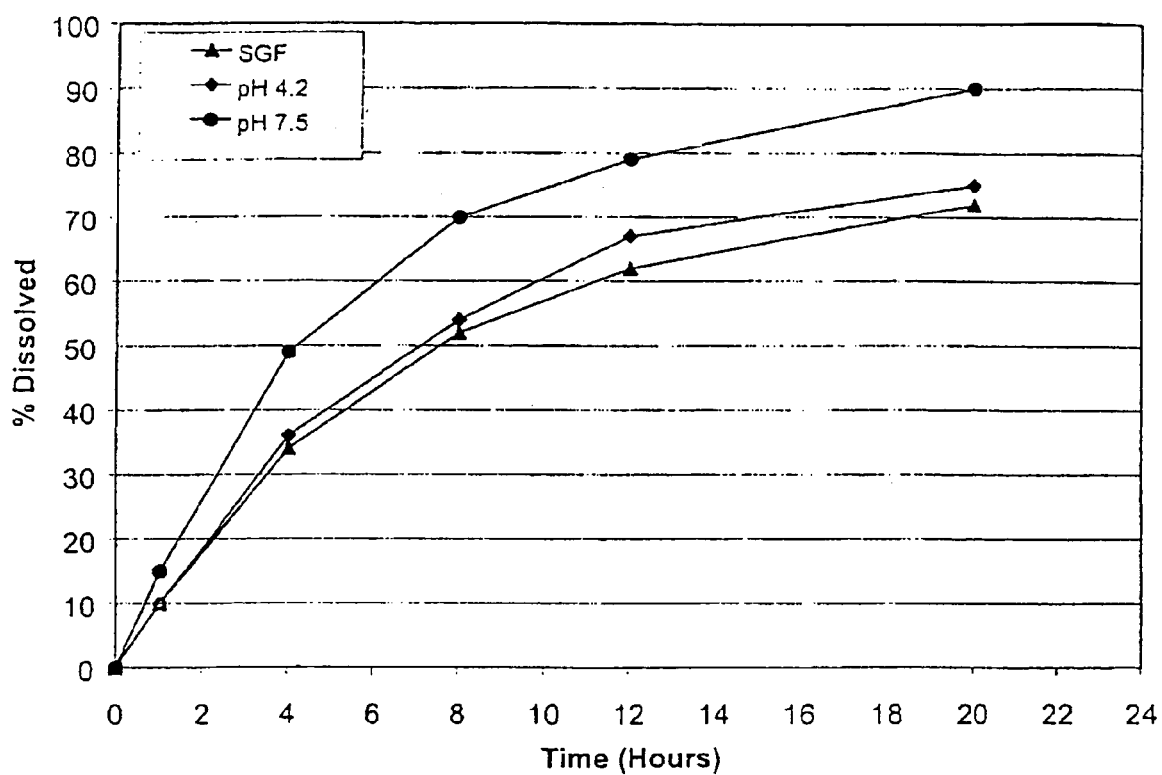

CONTROLLED RELEASE SODIUM VALPROATE FORMULATION

FIELD OF THE INVENTION

The invention is directed to controlled release formulations containing valproic acid, salts thereof (e.g., sodium valproate), amides thereof (e.g., valpromide), or derivatives thereof (e.g., divalproex sodium) which are suitable for administration to a patient in need of treatment related thereto. More specifically, the present invention relates to an oral dosage form comprising sodium valproate.

BACKGROUND OF THE INVENTION

Valproic acid, salts thereof, amides thereof, and derivatives thereof are available for treating epilepsy. For example, sodium valproate is useful for treating epileptic phenomena. This drug is effective for its intended therapy, however, there are shortcomings associated with this drug. For instance, sodium valproate is hygroscopic and liquifies very rapidly. Additionally, the drug exhibits a short-half life that can lead to fluctuations in blood antiepileptic drug levels. These properties can interfere with the manufacture and release of the drug from a dosage form, and are drawbacks in the management of epilepsies and other disorders which may be treated with sodium valproate.

A relationship has been reported between epilepsy, affective illness and migraine. Although the three disorders are distinct, they all are paroxysmal dysregulations of the nervous system that partially overlap in their pharmacology. Valproic acid and its pharmaceutically acceptable salts have been found to be effective in treating all three syndromes, suggesting the presence of shared underlying pathophysiology.

Although valproic acid and its pharmaceutically acceptable salts have been shown to be effective in both the treatment and prevention of migraine, its mechanism of anti-migraine action is unclear. It is, however, believed that valproic acid increases brain gamma-aminobutyric acid (GABA) levels and in doing so may activate the GABA receptor and suppresses migraine-related events.

It will be appreciated by those skilled in the art that controlled or sustained release compositions employing a valproic acid, pharmaceutically acceptable salt thereof, amide thereof, or derivative thereof would be particularly useful in the treatment and prevention of migraine or for the treatment of those in clinical need of antiepileptic therapy.

OBJECTS AND SUMMARY OF THE INVENTION

It is an object of certain embodiments of the present invention to provide a method for treating and/or preventing migraine by administering to an individual in need of such treatment a therapeutically or prophylactically effective amount of valproic acid, a pharmaceutically acceptable salt thereof, amide thereof, or derivative thereof, in a dosage form described herein.

It is an object of certain embodiments of the present invention to provide a method for treating epilepsy by administering to an individual in need of such treatment a therapeutically effective amount of valproic acid, a pharmaceutically acceptable salt thereof, amide thereof, or derivative thereof, in a dosage form described herein.

It is an object of certain embodiments of the present invention to provide a method for treating affective illness (including unipolar, bipolar illness and acute mania) due to a variety of causes by administering to an individual in need of such treatment a therapeutically effective amount of valproic acid, a pharmaceutically acceptable salt thereof, amide thereof, or derivative thereof, in a dosage form described herein.

It is also a further object of certain embodiments of the present invention to provide a controlled release dosage form comprising a medicament such as valproic acid, a pharmaceutically acceptable salt thereof, amide thereof, or a derivative thereof, that can provide therapeutic levels of the medicament to an animal or human in need of such treatment over a twelve hour to twenty-four hour period.

It is an additional object of certain embodiments of the present invention to provide a controlled or sustained release formulation for valproic acid, pharmaceutically acceptable salt thereof, amide thereof, or derivative thereof, that provides a time to maximum plasma concentration ($T_{max}$) at from about 6 to about 20 hours and preferably at from about 6 hours to about 18 hours after administration of the formulation.

Other objects and features of this invention will be more apparent to those of ordinary skill in the art from the following specification, taken in conjunction with the drawings and the accompanying claims.

In accordance with the above-mentioned objects and others, the present invention in certain embodiments is directed to a controlled release oral dosage form comprising valproic acid, pharmaceutically acceptable salt thereof, amide thereof, or derivative thereof, that is suitable for providing once-a-day administration of the drug, wherein the dosage form provides a time to maximum plasma concentration ($T_{max}$) of the drug at from about 6 to about 20 hours and preferably at from about 6 hours to about 18 hours after administration.

In certain embodiments, the present invention is directed to a method for treating and/or preventing migraine by administering a therapeutically or prophylactically effective amount of valproic acid, a pharmaceutically acceptable salt thereof, amide thereof, or derivative thereof, in a dosage form described herein to an individual in need of such treatment.

In certain embodiments, the present invention is directed to a method for treating epilepsy and/or affective illness by administering a therapeutically effective amount of valproic acid, a pharmaceutically acceptable salt thereof, amide thereof, or derivative thereof, in a dosage form described herein to an individual in need of such treatment.

In certain embodiments, the controlled release oral dosage form of the present invention comprises:
  (a) a core comprising:
    (i) an active agent selected from the group consisting of valproic acid, pharmaceutically acceptable salt thereof, amide thereof, and derivative thereof; and
    (ii) a pharmaceutically acceptable carrier;
  (b) a membrane coating surrounding the core, said membrane being permeable to gastrointestinal fluid; and
  (c) at least one passageway in the membrane; and said dosage form providing time to maximum plasma concentration ($T_{max}$) of the drug at from about 6 to about 20 hours.

The core of the present invention is not a bilayer tablet core, and preferably is a matrix formulation having the active agent dispersed therein. The core can be immediate release or controlled release.

In certain embodiments, the controlled release oral dosage form of the present invention is preferably in the form of a tablet, capsule, or in any other suitable unit dosage form.

In certain embodiments, the dosage form comprising the valproic acid, pharmaceutically acceptable salt thereof, amide thereof, or derivative thereof is suitable for administration on a once-a-day basis. When administered on a once-a-day basis, the daily dose may vary, e.g., from about 50 mg to about 2000 mg, from about 100 mg to about 1000 mg, or from about 250 mg to about 600 mg, depending on the clinical needs of the patient. Such daily dose may be contained in one controlled-release dosage form of the invention, or may be contained in more than one such dosage form. For example, a controlled-release dosage form may be formulated to contain 100, 250 or 500 mg of the valproic acid; or pharmaceutically acceptable salt thereof, amide thereof, or derivative thereof that provides for 100, 250 or 500 mg of valproic acid; and a combination of these dosage forms may be administered together to provide a desired once-a-day valproic acid dose.

In certain embodiments of the present invention, the dosage form comprises a pharmaceutically acceptable salt of valproic acid. Such salt forms include, for example and without limitation, sodium valproate, potassium valproate, calcium valproate, and mixtures thereof. In certain preferred embodiments, the salt form is sodium valproate.

In certain embodiments of the present invention, the dosage form comprises a derivative of valproic acid. Such derivatives include, for example and without limitation, 2-propylpentanol-di-n-propylacetate, glycerol tri-dipropylacetate, divalproex sodium, and mixtures thereof.

In certain embodiments, the dosage form comprises a neutralized form of the divalproex sodium as described in U.S. patent application Ser. No. 09/785,069, the disclosure of which is hereby incorporated by reference. The neutralized form of divalproex sodium refers to divalproex sodium in which the valproic acid moiety has been neutralized by addition of a strong base, e.g., sodium hydroxide. Neutralized divalproex sodium is not an oligomer. Neutralized divalproex sodium also does not exhibit a 1:1 molar ratio of sodium valproate and valproic acid.

In certain embodiments of the present invention, the dosage form comprises an amide of valproic acid. An example of such an amide, is for example and without limitation, valpromide.

In certain preferred embodiments, the dosage form of the present invention comprises a pharmaceutically acceptable salt of valproic acid, preferably sodium valproate. When the drug used in the present invention is sodium valproate the controlled release solid oral dosage form containing such drug may also be referred to as "Sodium valproate XT".

In certain embodiments of the present invention, the membrane of the oral dosage form cracks within 1-5 hours after introduction to an aqueous medium to expose the core and increase the release rate. In certain alternate embodiments the membrane does not crack, but remains intact delivering the active agent through the passageway. In yet further embodiments, the active agent is released from the core through the passageway and from the core by the erosion or dissolution of the membrane.

In certain embodiments, the present invention is further directed to a method of manufacturing dosage forms described herein. In certain embodiments, the method of manufacture comprises granulating the active agent with a pharmaceutically acceptable carrier (e.g., lactose monohydrate, microcrystalline cellulose, or the like), optionally blending the granulation with a polymer, glidant and/or lubricant, compressing the blend to form tablet cores, optionally coating the cores with a seal coating, and then coating the seal coated cores with a membrane. In certain embodiments, the active ingredient may be granulated with a pharmaceutically acceptable polymer, optionally blended with glidant and lubricant to form tablet cores, optionally coating the cores with a seal coating, and then coating the seal coated cores with a membrane. More preferably, at least one passageway is drilled through the membrane of the oral dosage form or formed by indentations on the core. More preferably two passageways through the membrane.

Preferably, the membrane of the present invention is a semi-permeable membrane, denoting that the membrane is permeable to the passage of an exterior fluid, such as aqueous and biological fluid, in the environment of use, including the gastrointestinal tract. The membrane can also be a porous membrane.

The term "dosage form" as it is used herein means at least one unit dosage form of the present invention (e.g., the daily dose of the active ingredient can be contained in 2 unit dosage forms of the present invention for single once-a-day administration).

The term "sustained release" and "controlled release" are used interchangeably in this application and are defined for purposes of the present invention as the release of the drug from the dosage form at such a rate that when a once-a-day dose of the drug is administered in the sustained release or controlled-release form, blood (e.g., plasma) concentrations (levels) of the drug are maintained within the therapeutic range but below toxic levels over a period of time from about 12 to about 24 hours.

The term "$C_{max}$" as used herein, is the highest plasma concentration of the drug attained within the dosing interval after single administration, e.g., about 24 hours.

The term "$T_{max}$" as used herein, is the time period which elapses after administration of the dosage form at which the plasma concentration of the drug attains the highest plasma concentration of drug attained within the dosing interval, e.g., about 24 hours.

The term "$AUC_{0-t}$" as used herein, means area under the plasma concentration-time curve, as calculated by the trapezoidal rule over the time interval.

The term "single dose" means that the human patient has received a single dose of the drug formulation and the drug plasma concentration has not achieved steady state.

The term "multiple dose" means that the human patient has received at least two doses of the drug formulation in accordance with the dosing interval for that formulation (e.g., on a once-a-day basis). Patients who have received multiple doses of the controlled release formulations of the invention may or may not have attained steady state drug plasma levels, as the term multiple dose is defined herein.

The term "mean", when preceding a pharmacokinetic value (e.g. mean $T_{max}$) represents the arithmetic or geometric mean value of the pharmacokinetic value taken from a population of subjects.

BRIEF DESCRIPTION OF THE DRAWINGS

FIG. 1 is a graphical representation of the dissolution profile of sodium valproate XT tablets, 576 mg (equivalent to 500 mg valproic acid) in pH 7.5 phosphate buffer displaying original release data vs. release data (paddle method at 75 rpm). The original profile was generated from the dissolution testing of the batch after the batch was manufactured and the tablets were re-tested in ten months later to see if there was any significant change in the dissolution profile over a ten-month period. These profiles demonstrate that the formulation is stable with respect to dissolution.

FIG. 2 is a graphical representation of the dissolution profile of sodium valproate XT tablets, 576 mg in pH 7.5 phosphate buffer, using USP 24 Apparatus I (basket) at 100 rpm vs. Apparatus II (paddle) at 75 rpm. There were two reasons for changing the dissolution apparatus from paddle to basket, both of which stemmed from physical observation of the formulation of Example 1 and Depakote® ER tablets in phosphate buffer pH 7.5 over a period of 24 hours. It was observed that some of the Depakote® ER tablets got stuck at the bottom of vessels after gel matrix swelled up. This may contribute to underestimation of percent drug dissolved as the exposed surface area of tablet decreases. On the contrary, overestimation of percent drug dissolved from Example 1 tablets may occur as a result of tablets being hit by paddles when they became buoyant and started to rise to the top of vessels after partial release of drug inside. According to FIG. 2, dissolution of Example 1 tablets was slightly slower when Apparatus I was used, but not significant.

FIG. 3 is a graphical representation of the dissolution profile of tablets of the formulation of Example 1 and Depakote® ER tablets (divalproex sodium extended release tablet equivalent to 500 mg valproic acid) in pH 7.5 phosphate buffer. After 4 hours of dissolution, at least 20% more drug was released from tablets of Example 1 than from Depakote® ER tablets at all time points. It is believed to be due primarily to the differences in solubility of sodium valproate (2.5 g/ml) and divalproex sodium (1.27 mg/ml for valproic acid).

FIG. 4 is a graphical representation of the dissolution profile of Depakote® ER tablets, 500 mg in simulated gastric fluid (SGF), pH 4.2 acetate buffer and pH 7.5 phosphate buffer (basket method at 100 rpm).

FIG. 5 is a graphical representation of the dissolution profile of sodium valproate XT tablets, 576 mg in SGF, pH 4.2 acetate buffer and pH 7.5 phosphate buffer (basket method at 100 rpm).

From FIGS. 4 and 5, it is apparent that dissolution of drug from both tablets are pH dependent and the effects of pH are more pronounced in the case of Depakote® ER tablets.

DETAILED DESCRIPTION

The method and dosage forms of the present invention provide the advantage of treating human patients with a therapeutic amount of valproic acid, a pharmaceutically acceptable salt thereof, an amide thereof, or a derivative thereof, on a once-a-day basis which provides effective control of migraine headaches in human patients. In certain embodiments the dosage forms may be useful in the treatment of epilepsy and/or affective illness.

In certain preferred embodiments, the present invention provides a controlled release tablet comprising (a) a core comprising:
(i) an active agent selected from the group consisting of valproic acid, pharmaceutically acceptable salt thereof, amide thereof, and derivative thereof; and
(ii) a pharmaceutically acceptable polymer;
(b) a membrane coating surrounding the core; and
(c) at least one passageway in the membrane; and said dosage form providing time to maximum plasma concentration ($T_{max}$) of the drug at from about 6 to about 20 hours. Preferably the core comprises a pharmaceutically acceptable salt of valproic acid such as sodium valproate. In certain embodiments, the pharmaceutically acceptable polymer is capable of forming a hydrogel. Preferably the hydrogel (alone or in addition to the membrane) provides for the controlled release of the active agent.

In other alternate preferred embodiments, the present invention provides a controlled release tablet comprising (a) a core comprising:
(i) an active agent selected from the group consisting of valproic acid, pharmaceutically acceptable salt thereof, amide thereof, and derivative thereof; and
(ii) a pharmaceutically acceptable carrier;
(b) a membrane coating surrounding the core; and
(c) at least one passageway in the membrane; and said dosage form providing time to maximum plasma concentration ($T_{max}$) of the drug at from about 6 to about 20 hours. Preferably the core comprises a pharmaceutically acceptable salt of valproic acid such as sodium valproate. Preferably the membrane provides the controlled release of the active agent.

In certain alternate preferred embodiments, the present invention provides a controlled release tablet comprising (a) a core comprising:
(i) an active agent selected from the group consisting of valproic acid, pharmaceutically acceptable salt thereof, amide thereof, and derivative thereof; and
(ii) an osmotically active compound;
(b) a membrane coating surrounding the core; and
(c) at least one passageway in the membrane; and said dosage form providing time to maximum plasma concentration ($T_{max}$) of the drug at from about 6 to about 20 hours. Preferably the core comprises a pharmaceutically acceptable salt of valproic acid such as sodium valproate. Preferably, the osmotically active compound is coated with a pharmaceutically acceptable polymer, preferably a water insoluble polymer or enteric polymer such as, e.g., cellulose acetate phthalate.

In certain embodiments of the present invention, wherein the dosage form contains a pharmaceutically acceptable polymer, the pharmaceutically acceptable polymer is for example and without limitation, hydroxypropyl cellulose, hydroxypropylmethyl cellulose, methylcellulose, vinyl acetate/crotonic acid copolymers, maleic anhydride/methyl vinyl ether copolymers, polyalkylene oxide including but not limited to poly(ethylene) oxide, poly(methylene oxide), poly(butylene oxide); poly(hydroxy alkyl methacrylate); poly(vinyl) alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a hydrogel forming copolymer produced by forming a dispersion of a finely divided copolymer of maleic anhydride with styrene, ethylene, propylene, butylene or isobutylene cross-linked with from 0.001 to 0.5 moles of saturated cross-linking agent per mole of maleic anyhydride in the copolymer; Carbopol® acidic carboxy polymers having a molecular weight of 450,000 to 4,000,000; Cyanamer® polyacrylamides; cross-linked water swellable indenemaleic anhydride polymers; Goodrite® polyacrylic acid having a molecular weight of 80,000 to 200,000; starch graft copolymers; Aqua-Keeps® acrylate polymer polysaccharides composed of condensed glucose units such as diester cross-linked polyglucan and the like. Other polymers which form hydrogels are described in U.S. Pat. Nos. 3,865,108; 4,002,173 and 4,207,893 all of which are incorporated by reference. Mixtures of the aforementioned pharmaceutically acceptable polymers may also be used. In certain preferred embodiments the pharmaceutically acceptable polymer in combination with the drug is capable of forming a drug matrix for the controlled delivery of the drug.

In certain embodiments, the pharmaceutically acceptable polymer is a water insoluble polymer including, for example and without limitation, ethylcellulose, cellulose acetate, cellulose propionate, cellulose acetate propionate, cellulose acetate butyrate, cellulose acetate phthalate, cellulose triacetate, polymethyl methacrylate, polyethyl methacrylate, polybutyl methacrylate, polyisobutyl methacrylate, polyhexyl methacrylate, poly isodecyl methacrylate, polylauryl methacrylate, polyphenyl methacrylate, polymethyl acrylate, polyisopropyl acrylate, polyisobutyl acrylate, polyoctadecyl acrylate, polyethylene, polypropylene, polyethylene oxide, polyethylene terephthalate, polyvinyl isobutyl ether, polyvinyl acetate, polyvinyl chloride, polyurethane or a mixture thereof.

In certain preferred embodiments, the pharmaceutically acceptable polymer is hydroxypropylmethylcellulose, hydroxypropylcellulose, or mixtures thereof.

In preferred embodiments, the valproic acid, pharmaceutically acceptable salt thereof, amide thereof, or derivative thereof, and the polymer are at least partially interdispersed. In certain embodiments, the valproic acid, derivative or pharmaceutically acceptable salt thereof and the polymer comprise a homogenous mixture having a uniform dispersion.

Pharmaceutically acceptable carriers for use in the present invention include, are for example and without limitation, calcium phosphate dihydrate, calcium sulfate dihydrate, microcrystalline cellulose, cellulose derivatives, dextrose, lactose, anhydrous lactose, spray-dried lactose, lactose monohydrate, mannitol, starches, sorbitol and sucrose and mixtures thereof. Further examples of carriers include hydroxypropylmethylcellulose, hydroxypropylcellulose, methyl cellulose, carboxymethyl cellulose, sodium carboxymethyl cellulose, polyvinylpyrrolidone, polyethyleneglycol, cellulose acetate butyrate, hydroxyethyl cellulose, ethyl cellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanyhydrides, polyvinyl chloride, polyvinyl acetate, ethylene vinyl acetate, lectins, carbopols, silicon elastomers, polyacrylic polymers, maltodextrins, fructose, inositol, trehalose, maltose raffinose, and alpha-, beta-, and gamma-cyclodextrins, and suitable mixtures of the foregoing. A preferred pharmaceutically acceptable carrier is lactose monohydrate.

In certain embodiments, wherein the dosage forms of the present invention include an osmotically active compound, osmotically active compounds comprise a member selected from the group consisting of osmotic salts, such as sodium chloride, potassium chloride, magnesium sulfate, lithium phosphate, lithium chloride, sodium phosphate, potassium sulfate, sodium sulfate, potassium phosphate, osmotic carbohydrates; glucose, fructose, maltose and sorbitol; urea; osmotic acids; tartaric acid; citric acid; potassium acid phosphate; mixtures thereof and the like. Preferably the osmotic salt is citric acid.

In certain preferred embodiments, the osmotic salt is coated with a hydrophobic or enteric coating described herein. Certain preferred enteric coatings are cellulose acetate phthalate, ethylcellulose phthalate, hydroxypropyl methylcellulose succinate, cellulose acetate succinate, hydroxypropyl methylcellulose hexahydrophthalate, cellulose acetate hexahydrophthalate, hydroxypropyl methylcellulose trimellitate, and methacrylic acid/methacrylate copolymer (acid number 300 to 330, also known as Eudragit L®, available from Rohm & Haas), either alone or in admixture with one another.

The core may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-bis (B-aminoethyl ether)-N,N,N,N-tetraacetic acid (EGTA). The absorption enhancer comprises approximately 0 to about 20% of the total weight of the core and most preferably about 2% to about 10% of the total weight of the core.

In addition to the above ingredients, the core may also contain suitable quantities of other materials, e.g. preservatives, diluents, stabilizers, solubilizing agents, antioxidants, lubricants, binders, disintegrants, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the *Handbook of Pharmaceutical Excipients*, American Pharmaceutical Association (1986), incorporated by reference herein.

The binding agent may be any conventionally known pharmaceutically acceptable binder such as acacia, cellulose derivatives, gelatin, glucose, sodium alginate and alginate derivatives, sorbitol, starch, polyvinyl pyrrolidone, hydroxypropyl cellulose, hydroxypropyl methylcellulose, hydroxyethyl cellulose, ethylcellulose, polymethacrylate, waxes and the like. Mixtures of the aforementioned binding agents may also be used. The preferred binding agents are water soluble such as polyvinyl pyrrolidone having a weight average molecular weight of 25,000 to 3,000,000. The binding agent comprises approximately about 0 to about 40% of the total weight of the core and preferably about 3% to about 15% of the total weight of the core.

Prior to compressing the granules, the conventional solid pharmaceutical diluents such as microcrystalline cellulose, lactose, dextrose and the like may be added to the mixture of granulations in amounts from about 0 to 60% weight based on the weight of the compressed, uncoated tablet.

Examples of lubricants are magnesium stearate, glyceryl monostearate, stearic acid, glycerylbehaptate, polyethylene glycol, calcium stearate, oleic acid, caprylic acid, magnesium isovalerate, calcium laurate, magnesium palmitate, behenic acid, glyceryl behenate, glyceryl stearate, zinc stearate, ethylene oxide polymers (for example, available under the registered trademark Carbowax from Union Carbide, Inc., Danbury, Conn.), sodium lauryl sulfate, magnesium lauryl sulfate, sodium oleate, sodium stearyl fumarate, DL-leucine, colloidal silica, and others as known in the art. The lubricant will be in the range of 0 to about 4 percent, and preferably 0 to about 2.5 percent by weight of the compressed, uncoated tablet.

Glidants may also be added to the formulation to improve the flow characteristics of the granulation. Examples of suitable glidants include, for example and without limitation, talc, silicon dioxide, and cornstarch.

Prior to coating the core with the membrane, the core may be indented. The indentation can be made during compression by an indentation pin located on the press punch. Alternatively, the core can be indented after compression. By "indented" it is meant that there is a depression in the core of the present invention.

Prior to coating the core with a membrane, the core may be coated with a pharmaceutically acceptable film-coating, e.g., for stability purposes (e.g., coated with a moisture barrier) or for process purposes. For example, the core may be overcoated with a film coating, preferably containing a pigment and a barrier agent, such as hydroxypropylmethylcellulose and/or a polymethylmethacrylate. An example of a suitable material which may be used for such a hydrophilic coating is hydroxypropylmethylcellulose (e.g., Opadry® or Opadry AMB, both commercially available from Colorcon, West Point, Pa.), or Collicoat. The film coating may also include sodium chloride. Optionally the core may be overcoated with Povidone K30 and PEG 3350 or other materials of the like. Any pharmaceutically acceptable manner known to those skilled in the art may be used to apply the coatings. For example, the coating may be applied using a coating pan or a fluidized bed. An organic, aqueous or a mixture of an organic and aqueous solvent is used for the hydrophobic polymer or enteric coating. Examples of suitable organic solvents are, e.g., isopropyl alcohol, ethanol, and the like, with or without water. Aqueous solvents are preferred for the overcoating procedures. In certain embodiments, the pharmaceutically acceptable film-coating around the core, e.g., for stability purposes, does not affect the release of the active agent from the core. In certain preferred embodiments, the pharmaceutically acceptable film-coating around the core, e.g., for stability purposes, does not substantially affect the release of the active agent from the core (e.g. the mean dissolution of the dosage form with a film-coated core is ±15% the mean dissolution of dosage form with a non-film coated core).

The core is further coated with a membrane, preferably a polymeric membrane to form the controlled release tablet of the invention. In preferred embodiments the membrane is permeable to passage of external fluid such as water and biological fluids and to the passage of the drug of the core. In certain alternate embodiments, the membrane is a semi-permeable membrane. Materials that are useful in forming the membrane are alkylcelluloses (e.g., ethylcellulose), cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,112,10 which are incorporated herein by reference. The most preferred membrane material is cellulose acetate comprising an acetyl content of 39.3 to 40.3%, commercially available from Eastman Fine Chemicals.

In an alternative embodiment, the membrane can be formed from the above-described polymers and a flux enhancing agent. The flux enhancing agent increases the volume of fluid imbibed into the core to enable the dosage form to dispense substantially all of the valproic acid, derivative or pharmaceutically acceptable salt thereof through the passageway and/or the porous membrane. The flux enhancing agent can be a water soluble material or an enteric material. Some examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methycellulose, hydroxyprophy methycellulose phthalate, cellulose acetate phthalate, polyvinyl alcohols, methacrylic acid copolymers, polaxamer (e.g., Lutrol®, commercially available from BASF), and mixtures thereof. The preferred flux enhancer is PEG 400.

The flux enhancer may also be a drug that is water soluble or a drug that is soluble under intestinal conditions. If the flux enhancer is a drug, the present dosage form has the added advantage of providing an immediate release of the drug which is selected as the flux enhancer.

In certain embodiments, the flux enhancing agent comprises approximately 0 to about 40% of the total weight of the coating, most preferably about 2% to about 20% of the total weight of the coating. The flux enhancing agent dissolves or leaches from the membrane to form paths in the membrane for the fluid to enter the core and dissolve the active ingredient.

In addition, the membrane can be formed with enteric material. As enteric coating material polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac, zein or other suitable enteric coating layer polymer(s). Some preferred commercial enteric coating materials are EUDRAGIT® L 100-55, EUDRAGIT® L 30 D-55, EUDRAGIT® L 100, and EUDRAGIT® S 100.

The enteric coating material comprises approximately 0 to about 60% of the total weight of the coating, most preferably about 2% to about 40% of the total weight of the coating.

In certain embodiments, the membrane may also comprise commonly known excipients such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 2% to about 15% of the plasticizer can be used based upon the total weight of the coating. In certain preferred embodiments, the plasticizer is triacetin.

The membrane may be further coated with a pharmaceutically acceptable film-coating, e.g., for stability purposes (e.g., coated with a moisture barrier) or for process purposes. For example, the membrane may be overcoated with a film coating, preferably containing a pigment and a barrier agent, such as hydroxypropylmethylcellulose and/or a polymethylmethacrylate. An example of a suitable material which may be used for such a hydrophilic coating is hydroxypropylmethylcellulose (e.g., Opadry®, commercially available from Colorcon, West Point, Pa.). In addition, other suitable materials are Povidone K30, PEG 3350, or the like. Any pharmaceutically acceptable manner known to those skilled in the art may be used to apply the coatings. For example, the coating may be applied using a coating pan or a fluidized bed. An organic, aqueous or a mixture of an organic and aqueous solvent is used for the hydrophobic polymer or enteric coating. Examples of suitable organic solvents are, e.g., isopropyl alcohol, ethanol, and the like, with or without water. Aqueous solvents are preferred for the overcoating procedures. In certain preferred embodiments, the pharmaceutically acceptable film-coating around the membrane does not affect, or does not substantially affect the release of the active agent from the dosage form.

In certain preferred embodiments of the present invention, the oral dosage form contains at least one passageway in the membrane. As used herein the term passageway includes an aperture, orifice, bore, hole, weaken area or an erodible element such as a gelatin plug that erodes to form an osmotic passageway for the release of the valproic acid, pharmaceutically acceptable salt thereof, amide thereof, or derivative thereof from the dosage form. A detailed description of the passageway can be found in such as U.S. Pat. Nos. 3,845,770, 3,916,899, 4,034,758, 4,063,064, 4,077,407, 4,088,864, 4,783,337 and 5,071,607 (the disclosures of which are hereby incorporated by reference).

In certain embodiments the passageway can be formed by drilling, including mechanical and laser drilling, through the membrane. Passageways and equipment for forming passageways are disclosed in U.S. Pat. Nos. 3,845,770, 3,916,899, 4,063,064, and 4,088,864. In certain preferred embodiments, a passageway is drilled in each side of the tablet.

In other embodiments, the passageway is formed by making an indentation onto the core prior to the membrane coating to form a weakened area of the membrane at the point of the indentation.

In certain embodiments, the membrane coating around the core is less than 10% of the total weight of the dosage form, preferably the membrane coating around the core will be from about 1% to about 7%, preferably from about 2% to about 6%, most preferably from about 3% to about 5% based on the total weight of the formulation.

In certain embodiments, the membrane is permeable to aqueous fluids or gastrointestinal fluids, but not to the active agent. Thus, in certain embodiments, the drug is release through the at least one hole or passageway in the membrane.

In certain alternate embodiments, the membrane is permeable to both aqueous solutions or gastrointestinal fluids and to the active agent. Thus, the membrane is permeable to the active agent and drug is released through a hole or passageway and through the membrane in solution or in vivo.

In an certain embodiments, the dosage form of the present invention may also comprise an effective amount of the drug that is available for immediate release. The effective amount of drug available for immediate release may be coated onto the membrane or the dosage form or it may be incorporated into the membrane.

In certain preferred embodiments, the release of the drug from the dosage form is controlled by both the pharmaceutically acceptable polymer of the core and the membrane surrounding the core. Preferably, upon contact with environmental fluids which permeate through the membrane, the polymer forms a hydrogel which controls the release of the drug from the dosage form.

In certain embodiments, the core comprising the drug and polymer is in the form of a matrix which controls the release of the drug from the dosage form alone, or controls the release of the drug in combination with the membrane and at least one passageway therein.

In certain preferred embodiments, the drug is released from the dosage form is controlled by both the pharmaceutically acceptable polymer of the core and the membrane surrounding the core and is suitable for once-a-day therapy.

In certain embodiments the dosage forms of the present invention are prepared by wet granulating the valproic acid, pharmaceutically acceptable salt thereof, amide thereof, or derivative thereof with the pharmaceutically acceptable polymer, pharmaceutically acceptable carrier, and/or osmotically active compound. The formulations may be prepared by granulating with an aqueous or organic solvent as known in the art. Optionally, a pharmaceutically acceptable diluent may be included in the granulation. Thereafter, the granules may be blended with additional excipients, including, e.g., lubricants, glidants, etc. The granulation is then compressed into a tablet core. Thereafter, the granulation is optionally seal coated with a film forming polymer such as hydroxypropyl cellulose, hydroxypropylmethyl cellulose, cellulose esters or ethers, an acrylic polymer or mixture thereof. The coating solution may comprise an aqueous or organic solvent. The seal coated tablet is then coated with a membrane which is permeable to an exterior fluid. Additionally, one or more passageways may be drilled through the membrane wall. Alternatively, the passageway may be formed in situ by incorporating leachable pore forming materials in the wall.

Alternatively, the dosage form of the present invention is prepared by other granulating techniques known in the art. For example, the valproic acid, pharmaceutically acceptable salt thereof, amide thereof, or derivative thereof may be spray granulated with the pharmaceutically acceptable polymer, pharmaceutically acceptable carrier, and/or osmotically active compound and an aqueous or organic solvent as known in the art. The granules may further include or be further blended with excipients as described herein, and compressed into tablet cores. The cores may be optionally coated with a seal coating. The core is further coated with a membrane as described herein, and one or more passageways may be drilled through the membrane wall. Alternatively, the passageway may be formed in situ by incorporating leachable pore forming materials in the wall.

In certain preferred embodiments, the controlled release solid oral dosage form exhibits the following dissolution profile when tested in pH 7.5 phosphate buffer, using USP 24 Apparatus I (basket) at 100 rpm: from 0 to about 50% of the drug released after 2 hours; from about 10 to about 70% of the drug released after 4 hours; from about 40 to about 90% of the drug released after 8 hours; greater than about 50% of the drug released after 12 hours; and greater than about 60% of the drug released after 20 hours.

In certain preferred embodiments, the controlled release solid oral dosage form exhibits the following dissolution profile when tested in pH 7.5 phosphate buffer, using USP 24 Apparatus I (basket) at 100 rpm: from about 10 to about 40% of the drug released after 2 hours; from about 20 to about 60% of the drug released after 4 hours; from about 55 to about 85% of the drug released after 8 hours; greater than about 65% of the drug released after 12 hours; and greater than about 70% of the drug released after 20 hours.

In certain embodiments, the controlled release solid oral dosage form exhibits the following dissolution profile when tested in simulated gastric fluid (SGF) using USP 24 Apparatus I (basket) at 100 rpm: from 0 to about 35% of the drug released after 2 hours; from about 20 to about 65% of the drug released after 4 hours; from about 30 to about 80% of the drug released after 8 hours; greater than about 40% of the drug released after 12 hours; greater than about 50% of the drug released after 20 hours.

In certain embodiments, the controlled release solid oral dosage form exhibits the following dissolution profile when tested in pH 4.2 acetate buffer using USP 24 Apparatus I (basket) at 100 rpm: from 0 to about 35% of the drug released after 2 hours; from about 20 to about 65% of the drug released after 4 hours; from about 30 to about 80% of the drug released after 8 hours; greater than about 40% of the drug released after 12 hours; greater than about 50% of the drug released after 20 hours.

DESCRIPTION OF CERTAIN PREFERRED EMBODIMENTS

The following example illustrates various aspects of the present invention. It is not to be construed to limit the claims in any manner whatsoever.

Example 1

Sodium Valproate XT, 576 mg tablet formulations (eq. to 500 mg valproic acid) were prepared and are listed in Table 1.

TABLE 1

| Ingredient | mg/tablet | % w/w |
|---|---|---|
| Sodium Valproate Granules | | |
| Sodium Valproate, EP | 576.11 | 69.91 |
| Lactose Anhydrous, USP | 134.68 | 16.34 |
| Hydroxypropyl Cellulose, NF (Klucel EF) | 37.41 | 4.54 |
| Ethanol-SDA 3A 190 Proof | * | * |
| Sub-total: | 748.20 | 90.79 |
| Sodium Valproate Tablets, 576 mg (Uncoated) | | |
| Sodium Valproate Granules | 748.02 | 90.79 |
| Colloidal Silicon Dioxide, NF (Cab-O-Sil M5) | 11.51 | 1.40 |
| Magnesium Stearate, NF/FCC | 7.67 | 0.93 |
| Sub-total: | 767.20 | 93.12 |
| Sodium Valproate Tablets, 576 mg (Seal Coated) | | |
| Sodium Valproate Tablets, 576 mg (Uncoated) | 767.20 | 93.12 |
| Hydroxypropyl Methylcellulose, USP (Methocel E5) | 11.86 | 1.44 |
| Hydroxypropyl Cellulose, NF (Klucel EF) | 11.86 | 1.44 |
| Ethanol-SDA 3A 190 Proof | * | * |
| Sub-total: | 790.92 | 96.00 |
| Sodium Valproate XT Tablets, 576 mg (CA Coated) | | |
| Sodium Valproate Tablets, 576 mg (Seal Coated) | 790.92 | 96.00 |
| Cellulose Acetate 398-10, NF | 28.01 | 3.40 |
| Triacetin, USP | 1.65 | 0.20 |
| Polyethylene Glycol 400, NF | 3.30 | 0.40 |
| Acetone, NF | * | * |
| Total: | 823.88 | 100.00 |

* Evaporated during processing.
** Used to adjust the batch size to obtain optimum load.
(a) Total batch size for the specified step only. Solvent weight is not included in calculation of batch size as it is evaporated during processing.
(b) Total batch size for the specified step only.

The tablets of having the formulation table 1 are prepared as follows:

(a) Granulation:

0.324 kg of lactose (anhydrous) and 1.386 kg of sodium valproate are delumped by pass through a 40 mesh screen and then mixed. 0.9 kg of hydroxypropyl cellulose (Klucel EF) is dissolved in 1.41 kg of ethanol SDA 3A 190 Proof. The delumped materials are then transferred to fluidized bed granulator and granulated by spraying with the granulation solution using the following conditions: product temperature: 25-35° C.; atomization air pressure: 1-3 bar; spray rate 10-150 mL/min. Once the granulation solution is consumed, granules are dried in the fluidized bed coater until the loss of drying is less than 2%. The dried granules are then passed through the Comil equipped with a screen equivalent to 18 mesh.

(b) Blending and Compression 4.387 kg of sodium valproate granules are then blended with 0.0675 kg of colloidal dioxide in V-blender for five minutes followed by blending with magnesium stearate with five minutes. The resulting blend is then compressed into 767.2 mg weight tablets on a rotary press fitted with 15/32" round standard concave punches.

(c) Seal Coating (Optional)

The tablets are seal coated with an Opadry material or other suitable water soluble materials. 0.030 kg of hydroxypropyl methylcellulose (Methocel E-5) and 0.30 kg of hydroxy propyl cellulose (Klucel EF) were dissolved in 0.69 kg of ethanol-SDA 3A 190 Proof. The resulting solution is then sprayed onto the tablets using a pan coater under the following conditions: exhaust air temperature 25-35° C.; atomization air pressure 25-35 psi; spray rate of 10-50 mL/min and air volume of 200-400 SCFM. The tablets are applied with the seal coating until a 3% theoretical coating level of approx. 3% is achieved.

(d) Sustained Release Coating

The cellulose acetate is dissolved in acetone while stirring with an homogenizer. The polyethylene glycol 400 and triacetin are then added to the cellulose acetate solution and mixed until a homogeneous solution is obtained. The coating solution is then sprayed onto the seal coated tablets in fluidized bed coater employing the following conditions: Product temperature 16-24° C.; atomization air pressure of 1-2 bar; and a spray rate of 10-30 mL/min. This coating was continued until a theoretical coating level of approximately 5% is reached. The coated tablets are then dried in the fluidized bed coater for approximately 10 minutes. One orifice is then either mechanically drilled or laser drilled onto each side of the sustained release tablets.

The CA Coated tablets of Example 1 were compared to Depakote® DR and Depakote® ER in two separate two-period crossover biostudies in eight healthy volunteers in fed and fasted conditions. The mean pharmacokinetic parameters for these studies are summarized in Tables 2 and 3.

TABLE 2

| Condition | Parameters | Example 1 | Depakote DR | G-Mean Ratio | A-Mean Ratio |
|---|---|---|---|---|---|
| Fasting | $C_{max}$ (μ/mL) | 22.01(17.13) | 47.76(14.04) | 0.459 | 0.464 |
| | $AUC_{0-t}$ (μ · hr/mL) | 626.1 | 777.65 | 0.805 | 0.857 |
| | $T_{max}$ (hr) | 9.88 | 15.70 | ** | ** |
| Fed | $C_{max}$ (μ/mL) | 35.90(30.83) | 46.40(16.29) | 1.065 | 0.774 |
| | $AUC_{0-t}$ (μ · hr/mL) | 849.72(29.25) | 908.13(36.49) | 1.004 | 0.936 |
| | $T_{max}$ (hr) | 7.00 | 10.00 | ** | ** |

** Not Determined

TABLE 3

| Condition | Parameters | Example 1 | Depakote DR | G-Mean Ratio | A-Mean Ratio |
|---|---|---|---|---|---|
| Fasting | $C_{max}$ (µ/mL) | 24.00(21.71) | 21.39(41.16) | 1.219 | 1.303 |
|  | $AUC_{0-t}$ (µ·hr/mL) | 650.59(23.57) | 600.94(54.84) | 1.348 | 1.816 |
|  | $T_{max}$ (hr) | 8.50(32.68) | 16.50(52.14) | 0.590 | 0.771 |
| Fed | $C_{max}$ (µ/mL) | 33.45(27.83) | 29.04(26.19) | 1.148 | 1.181 |
|  | $AUC_{0-t}$ (µ·hr/mL) | 742.73(18.81) | 724.59(15.79) | 1.021 | 1.023 |
|  | $T_{max}$ (hr) | 10.25(40.65) | 18.38(33.67) | 0.548 | 0.604 |

** Not Determined

Example 2

In Example 2, a controlled release tablet containing 576 mg of sodium valproate was prepared as follows:

(A) Citric Acid (Enteric Coated)

| Ingredient | % w/w | kg |
|---|---|---|
| Citric acid anhydrous (Fine granular) | 90.00 | 18.00 |
| Cellulose acetate phthalate | 7.144155.56 | 1.429 |
| Talc (ALTALC 500V) | 1.428 | 0.286 |
| Polyethylene glycol 400 | 1.428 | 0.286 |
| Purified Water | ** | 3.802 |
| Acetone | ** | 34.217 |

** Evaporated during processing

Cellulose acetate phthalate is dissolved in acetone while mixing with a homogenizer. Polyethylene glycol 400 is dissolved in purified water and the solution is added to the cellulose acetate phthalate solution. Talc is then added to the solution and mixed until it is homogeneously dispersed. Citric acid anhydrous (fine granular) is transferred to the fluidized bed coater and sprayed with the coating solution using the following conditions: product temperature 27-33° C.; atomization air pressure on 1.8-3.0 bars; air volume: 200-500M³/hr and spray rate of 20-100 mL/min. Once the coating solution is consumed, the resulting pellets are dried until the loss on drying is less than 1.5%. The coated pellets were then passed through the Sweco equipped with a #25 and #60 mesh screens.

(b) Granulation

| Ingredient | mg/tablet | % w/w |
|---|---|---|
| Sodium Valproate | 576.11 | 76.31 |
| Citric Acid (CAP coated) | 155.56 | 20.60 |
| Klucel EF | 23.33 | 3.09 |
| Ethanol-SDA 3A 190 Proof | * | * |
| Total Solid | 755 | 100.00 |

* Evaporated during processing

Hydroxypropyl cellulose (Klucel EF) is dissolved in ethanol and the resulting solution is used to granulate the sodium valproate and citric acid (enteric coated) blend in the fluidized bed coater employing the following conditions: product temperature 27-35° C.; atomization air pressure on 1.0-2.0 bars; and spray rate of 5-20 mL/min. Once the coating solution is consumed, the resulting pellets are dried until the loss on drying is less than 1.5%.

(c) Blending and Compression

| Ingredient | mg/tablet | % w/w |
|---|---|---|
| Sodium Valproate Granules | 755.00 | 98.05 |
| Cabosil M5 | 9.22 | 1.20 |
| Magnesium Stearate | 5.78 | 0.75 |
| Total Solid | 770.00 | 100.00 |

Sodium valproate granules are then blended with colloidal silicon dioxide and magnesium stearate as given in Example 1. The resulting blend is then compressed into 770 mg tablets on a rotary press fitted with 7/16" or 1/2" round standard concave punches respectively.

(d) Seal Coating (Optional)

| Ingredient | % w/w |
|---|---|
| Sodium Valproate Tab (uncoated) | 95.00 |
| Placebo | ** |
| Opadry Clear (YS-1-7006) | 4.25 |
| Magnesium Stearate | 0.75 |
| Ethanol-SDA 3A 190 Proof | * |
| Total Solid | 100.00 |

* Evaporated during processing.
** Used to adjust the batch size to obtain optimum load.

The core tablets are seal coated with a homogeneous suspension of Opadry Clear and magnesium stearate in ethanol in a pan coater under the following conditions: exhaust temperature 25-47° C.; atomization air pressure 10-20 psi; and spray rate from 5-20 mL/minute. The core tablets are seal-coated suspension until a theoretical coating level of 5% is achieved. The tablets were dried for additional ten minutes in the pan coater.

(e) Sustained Release Coating

| Ingredient | % w/w |
|---|---|
| Sodium Valproate Tab (seal coated) | 97.40 |
| Placebo (seal coated) | ** |
| Cellulose Acetate 398-10, NF | 2.080 |
| Lutrol F-68, NF | 0.520 |
| Acetone | * |
| Total Solid | 100.00 |

* Evaporated during processing.
** Used to adjust the batch size to obtain optimum load.

The cellulose acetate is dissolved in acetone while mixing with a homogenizer. The Lutrol F-68 is then added to the solution and stirred until a clear solution is obtained. The coating solution is then sprayed onto the seal-coated tablets in a fluidized bed coater employing the conditions outlined in example 1. One 0.5 mm orifice is drilled on each side of the tablet.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A controlled release oral dosage form consisting of:
   (a) a core consisting of a compressed homogeneous mixture, the compressed homogeneous mixture consisting of (i) an active agent selected from the group consisting of sodium valproate or divalproex sodium; (ii) about 3 to about 15% of a binder selected from the group consisting of polyvinyl pyrrolidone, hydroxypropyl cellulose, hydroxypropyl methycellulose and mixtures of the foregoing; (iii) about 0 to about 60% of a diluent; and (iv) about 0 to about 4% of a lubricant;
   (b) optionally a seal coating surrounding the core wherein the seal coating does not substantially affect the release of the active agent from the immediate release core;
   (c) a polymeric membrane coating surrounding the core or the seal coating if present consisting of: (i) cellulose acetate; (ii) about 2% to about 20% of a flux enhancing agent that is a water soluble material or an enteric material, said flux enhancing agent is selected from the group consisting of sodium chloride, potassium chloride, sucrose, sorbitol, mannitol, polyethylene glycol (PEG), propylene glycol, hydroxypropyl cellulose, hydroxypropyl methycellulose, hydroxypropyl methycellulose phthalate, cellulose acetate phthalate, polyvinyl alcohols, polaxamer, and mixture thereof; and (iii) about 2% to about 15% of a plasticizer, said membrane being permeable to gastrointestinal fluid and the membrane coating comprises about 2 to about 6% of the total weight of the dosage form;
   (d) at least one passageway disposed in said membrane; wherein said oral dosage form being suitable for providing once-a-day oral administration of the active agent, said dosage form provides a mean time to maximum plasma concentration ($T_{max}$) of said active agent at about 6 to about 20 hours after oral administration and which exhibits the following dissolution profile when tested in pH 7.5 phosphate buffer, using USP 24 Apparatus I (basket) at 100 rpm: from 10 to about 40% of the active agent released after 2 hours; from about 20 to 60% of the active agent release after 4 hours; from about 55 to 85% of the active agent released after 8 hours; greater then about 65% of the active agent released after 12 hours; and greater than about 75% of the active agent released after 20 hours and which also exhibits the following dissolution profile when tested in pH 4.2 acetate buffer using USP 24 Apparatus I (basket) at 100 rpm: from 0 to about 35% of the active agent released after 2 hours; from about 20 to 65% of the active agent release after 4 hours; from about 30 to 80% of the active agent released after 8 hours; greater then about 40% of the active agent released after 12 hours; and greater than about 50% of the active agent released after 20 hours.

2. The controlled release dosage form as defined in claim 1 wherein the membrane coating comprises about 3% to about 5% of the total weight of the dosage form.

3. The controlled release dosage form as defined in claim 1 wherein the diluent or selected from the group consisting of microcrystalline cellulose, lactose or dextrose.

* * * * *